United States Patent [19]
Dobes et al.

[11] 4,451,147
[45] May 29, 1984

[54] REFRACTOMETER

[76] Inventors: Karel Dobes, Fafnerstr. 8, D-8000 München; Peter Fuchs, Vimystr. 4, D-8050 Freising; Otmar Rudolf, Kantstr. 24, D-8000 München, all of Fed. Rep. of Germany

[21] Appl. No.: 276,515

[22] Filed: Aug. 31, 1981

[51] Int. Cl.³ .......................................... G01N 21/41
[52] U.S. Cl. .................................................. 356/135
[58] Field of Search ............................. 356/135, 136

[56] References Cited

U.S. PATENT DOCUMENTS

| | | | |
|---|---|---|---|
| 2,934,992 | 5/1960 | Goldberg | 356/135 |
| 3,279,309 | 10/1966 | Goldberg | 356/135 |
| 3,625,620 | 12/1971 | Goldberg | 356/135 |
| 3,650,631 | 3/1972 | Grässel et al. | 356/136 |

FOREIGN PATENT DOCUMENTS 1154651 9/1963 Fed. Rep. of Germany .
1140517 7/1957 France .

OTHER PUBLICATIONS

Kelly; J. C. et al., "Measurement of Refractive Index of a Transparent Film on a Refractive Substrate", Opitica Acta, Oct. 1959, pp. 339-343.
Vossberg, III; C. A., "Scanning Refractometer for In-line Density Measurements", TAPPI, vol. 58, No. 6, Jun. 1975, pp. 83-84.
Model 107, Refractomer, TIFO 9, Nov. 1961, p. 2.

*Primary Examiner*—Bruce Y. Arnold
*Attorney, Agent, or Firm*—Cushman, Darby & Cushman

[57] ABSTRACT

A refractometer for measuring refractive index of a media during a continuous process in which a light beam is directed to a prismatic body having a media surface contacting the boundary surface of the media and a mirror surface, the media surface reflecting a measurement light beam refracted by the media and the mirror surface a reference beam. The reference and media beams are directed to respective light detectors.

26 Claims, 8 Drawing Figures

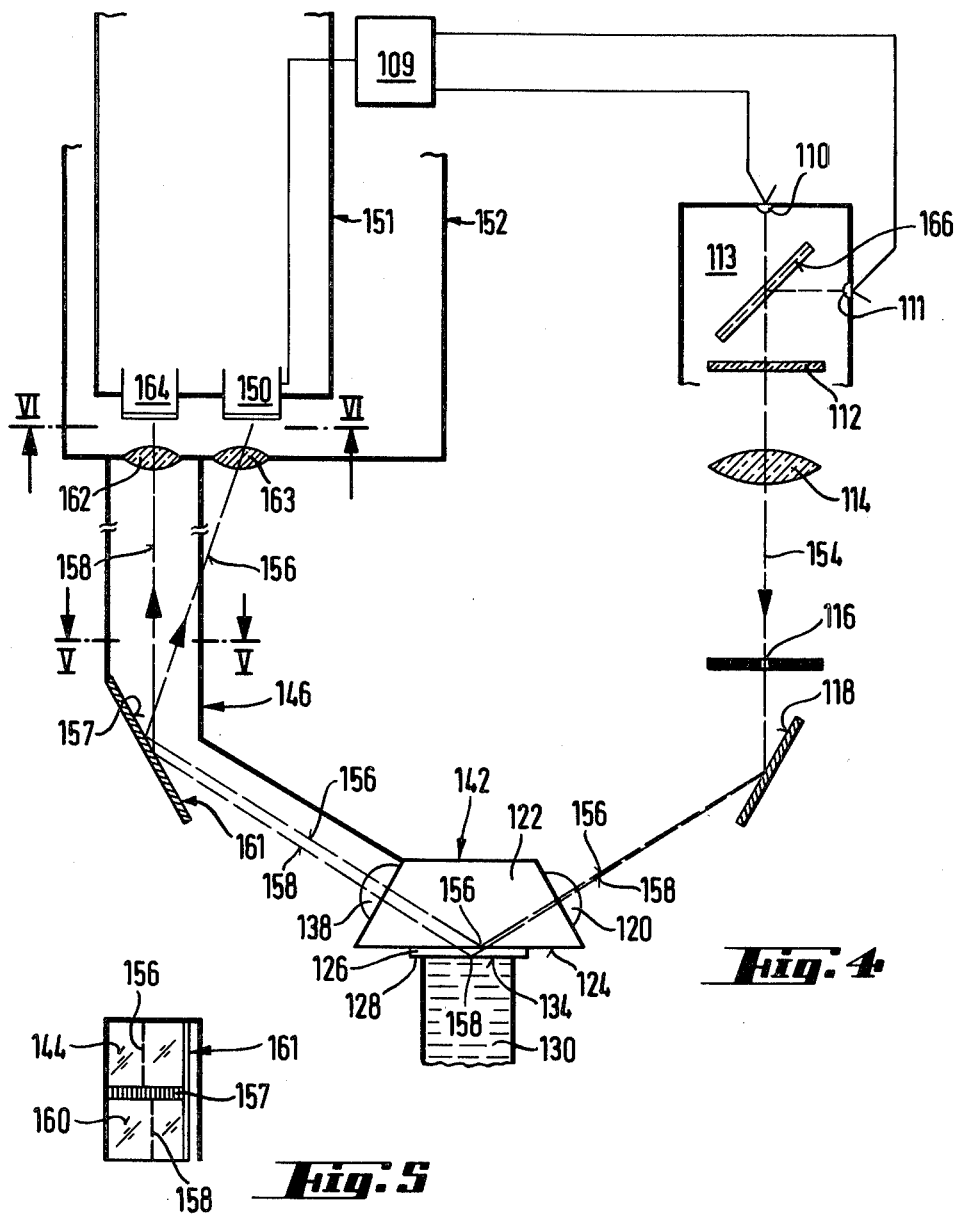

REFRACTOMETER

The instant invention relates to a refractometer, in particular for measurements during continuous processes. Such optical instruments for determining the refractive index and known as process refractometers serve for continuous measuring and for measuring in industrial processing engineering of gaseous and liquid media which must be examined constantly in respect of their invariable composition or mixture so that any erroneous process control can be corrected as soon as possible. To this end individual samples or preferably a moving flow of foodstuffs, for example fruit juices, beer, milk products, oils, etc. or chemicals like acids, polymers, liquid solutions etc, are brought into contact with the interface or boundary surface of an optical prism exposed to light. The light intensity, varying as the composition of the media varies, is detected in an apparatus which detects and evaluates the light received from the media, for instance a photocell. Corresponding measurement values are obtained by conversion in an electric circuit connected to the output end of the detecting apparatus.

DE-AS 23 06 091 describes an interference refractometer comprising as the means for examining the optical density of the flowing media a measuring cell, a comparing cell, and a means for detecting the resulting light interference. It is the object of this interference refractometer as, by the way, of all known refractometers, to eliminate the inaccuracy of the measured result which may be falsified quite considerably by temperature variations. It is suggested in this respect that the optical density of the flowing media remain constant until the corresponding resonance point be adjusted by means of a mechanical slide device, or that a control circuit be provided by means of which the variation of the spacing between the interferometer plates caused by temperature variations is eliminated, of that means be provided for periodically varying the length of two cells adapted to be tuned to each other.

All these devices and proposals suffer from the disadvantage that the separate treatment of reference light beams not only delays the process but also falsifies the measurement result.

Thus it is the object of the instant invention to design a refractometer of the kind specified initially such that temperature variations in the goods or medium to be measured will not have different influences on the reference light or on the light received from the media.

This object is met, in accordance with the invention, in that the boundary surface of the light prismatic body comprises a mirror surface area at which reference light beams are reflected. Advantageous further developments may be gathered from the claims.

A special advantage of the invention is seen in the fact that the reference light can be used for control of the light source, thereby automatically increasing the accuracy. Moreover, the solution proposed by the invention permits a compact structure since the light is passed through the arrangement in distinctly bundled and clear form. Further advantages will become obvious as the specification proceeds.

The invention will be described further, by way of example, with reference to the accompanying drawings, in which:

FIG. 4 is a view similar to FIG. 1 of another embodiment of the invention in which the light refracting wedge is replaced by a separating mirror device having a zero wedge angle;

FIG. 5 is a top plan view of the separating mirror device shown in FIG. 4 in a presentation similar to FIG. 3;

FIG. 6 is a front elevational view of a retaining means comprising a reference light receiver and a measuring light evaluator;

Figures 1, 2, 3:
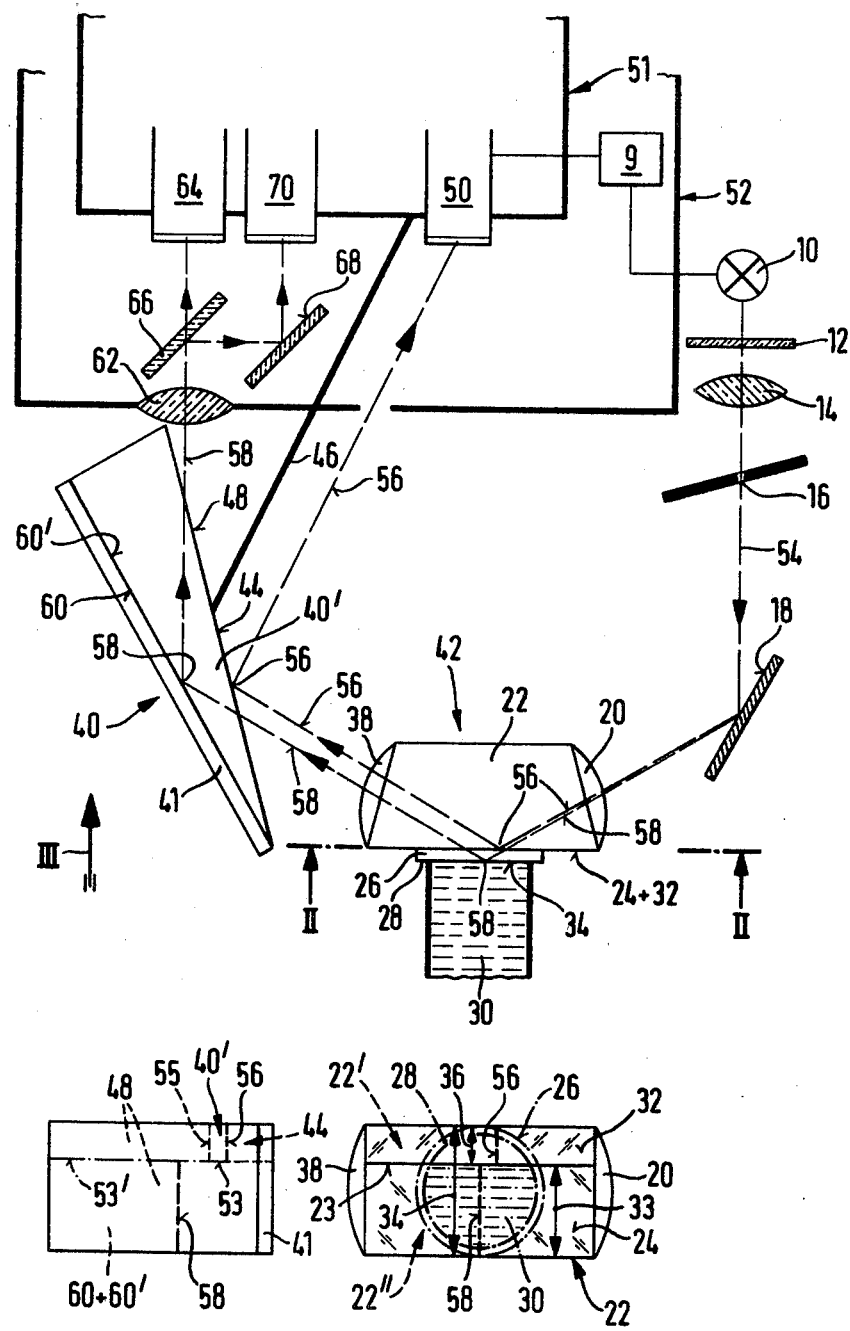
FIG. 1 is a top plan view of an arrangement showing the light path in particular through a light prismatic body in accordance with the invention and through a light refracting wedge in accordance with the invention.
FIG. 2 is a sectional view along the boundary surface at the light prismatic body in the arrangement of FIG. 1.
FIG. 3 is a view similar to FIG. 2 of the lower side of the light refracting wedge in the arrangement of FIG. 1.

As shown in FIG. 1, a light source 10 embodied by a wide spectrum halide lamp or an infrared diode, (i.e. a monochromatic light source) emits light through a ground glass disc 12, a convex lens 14, and a mask 16 on to a mirror 18 which introduces the light through a plane-convex input lens 20 into a prism 22. At a bottom or base area 24 of the prism there is provided a sapphire disc 26 secured by suitable glue such that, on the one hand, it is in plane-parallel abutment with the prism 22 and, on the other hand, it constitutes a free interface or boundary surface 28 at which the incident light beams from the light source 10 are deflected or refracted differently in correspondence with the variation in density of the medium 30 engaging or flowing past the boundary surface.

At its lower side the prism 22 comprises a mirror surface area 32 of rectangular, edge-like shape so that part of the incident light is reflected at this mirror surface area 32 without being influenced by the medium to be measured. The remaining active surface area 34 of the sapphire disc 26, on the other hand, causes different refraction or reflection of the light beams in accordance with the medium engaging or flowing past the boundary surface 28. Thus, the incident light beam is divided into a reference light beam in accordance with the reflection in the mirror surface area 32 and a measuring light beam in accordance with the refraction in the active surface area 34 of the sapphire disc 26.

Thus, if the goods to be measured or the flowing medium 30 displays variations in temperature because of changing process heat or other circumstances, the mirror surface area 32 is influenced by the temperature variations just like the active surface area 34 of the sapphire disc 26 because the active surface area 34 of the sapphire disc 26 extends into the mirror surface area 32 of the prism 22 through an overlapping surface area 36 and the entire active surface area 34, including the overlapping surface area 36 is exposed to the goods to be measured or to the flowing medium 30. For reasons of structural design the active surface area 34 usually is of somewhat smaller diameter than the sapphire disc 26. The boundary surface 28 and the mirror surface of the mirror surface area 32 thus lie in a plane-parallel plane.

Of course, an embodiment is conceivable which does not comprise the sapphire disc 26 and with which the mirror surface of the mirror surface area 32 is disposed at the lower side of the prism 22, the goods to be measured or the flowing medium 30 being admitted to a circular area of the base area 24 of the prism 22 corresponding, for instance, to the active surface area 34 including the overlapping surface area 36.

The light refracted by the boundary surface 28 thus consists in part of the reference light beam and the measuring light beam which leave the prism 22 through a plane-convex output lens 38 to impinge on a light refracting wedge 40.

The input lens 20 and the output lens 38 are connected with their plane sides to the corresponding faces of the prism 22, preferably by being glued to the same, and, together with the sapphire disc 26, they form a light prismatic body 42.

The light refracting wedge 40, preferably made of glass just like the light prismatic body 42, also comprises a rectangular partial mirror surface area 44 corresponding in width to the mirror surface area 32 at the base area 24 of the light prismatic body 42. The partial mirror surface area 44, however, does not extend across the full marginal zone of the light refracting wedge 40 at the side thereof which faces the light prismatic body 42 and from which the beams are incident which come from the light prismatic body 42. Instead it extends only up to a shield 46 so that the reference light beam coming from the mirror surface area 32 of the prismatic body 42 is reflected in the partial mirror surface area 44 at the upper side 48 of the light refracting wedge 40, reaching the corresponding reference light receiver 50 of an evaluator 52, uninfluenced by the shield 46.

The light beam 54 coming from the light source 10 is divided in the light prismatic body 42 not only into the reference light beam 56 but also into the measuring light beam 58 which passes through the light refracting glass wedge 40 to be reflected at the lower side 60 thereof, issuing from the upper side 48 of the light reflecting wedge 40, to be concentrated by a convex lens 62, and then reach a first measuring light receiver 64. In an advantageous further development another partly reflecting disc 66 is disposed in the light path of the measuring light beams 58 downstream of the convex lens 62. Preferably at a ratio of 50:50 the measuring light beams are passed to the first measuring light receiver 64 by this disc 66 and, on the other hand, they are reflected by another mirror 68 to reach a second measuring light receiver 70. This it is even possible to measure two components in the medium 30 under investigation at the receivers 64 and 70, depending on the downstream electronics.

It is within the limits of ordinary skill in the art to alter the optical beam path with regard to the lens system, mask system, and division of the measuring light beams in such manner that further components can be measured and calculated, if desired. The signals to be derived from the reference light receiver 50 serve not only for calculation purposes and ratio formation but are also utilized for control of the brightness of the light source 10.

As already mentioned, the light refracting wedge 40 having the partial mirror surface area 44 at the upper side 48 to deal with the reference light beam 56 and the mirror surface for the measuring light beam 58 at its lower side 60, preferably is preferably made of glass. If required, it may also be made of a material similar to glass, such as plastics of glass properties. This also applies to the light prismatic body 42 and any other lenses needed.

It may be observed in conclusion, as regards the optical arrangement, that temperature compensation is obtained because the reference light beam and the measuring light beam are both passed through the prism and thus exposed to the same temperature influences.

In the overall apparatus usually ultrasonic waves are applied intermittently to the measuring head containing the medium under examination or flowing through so as to loosen any impurities from the measuring surfaces by the ultrasonic vibrations and rinse off the flowing medium. An opto-electrical analog-digital converter is disposed in the apparatus behind the chamber housing the optical system. The apparatus preferably also is furnished with infrared diodes for the light source. Peltier elements preferably are provided to assure the correct temperature is maintained since critical electronic component parts, such as the photo-electronic measuring sensors should be operated at stable temperatures. A microprocessor is connected to the analog-digital converter to carry out all the control and regulating functions and, in the first place, process the measuring pulses and render them visible in multidigit displays. Within the limits of a modification of the first embodiment the light refracting wedge 40 is not given as a full wedge having a mirror surface and a light refracting surface but instead is limited to a width which corresponds to the mirror surface area 32 of the light prismatic body 42. In this manner the measuring light beam 58 does not pass through the light refracting wedge 40 but instead impinges on a light reflecting surface 60' which corresponds to the lower side 60 of the wedge 40. In other words, the light refracting wedge 40 is replaced by a part-wedge 40' mounted on a carrier 41, a replacement made within the skill in the art. In this event the part-wedge 40' must have a width approximately corresponding to that of the mirror surface area 32 of the light prismatic body 42. The maximum length of the part-wedge 40' must reach up to the shield 46. The remainder of the surface of the carrier 41 not covered by the part-wedge 40' and corresponding to the lower side 60 of the full wedge, must be designed as reflecting surface 60' in order that the measuring light beam 58 may be reflected at this reflecting surface to reach the measuring light receiver 64. Preferably the reflecting surface is designed to be a mirror surface. This means that in the embodiment in question the carrier 41 is a mirror on which the part-wedge 40' is mounted which is likewise provided with a mirror surface at the side remote from the mirror surface 60' and facing the prism 22, i.e. at the free side. Thus the reference light beam 56 is deflected at the mirror surface of the part-wedge 40' and the measuring light beam 58 at the mirror surface 60'.

It is likewise within the usual skill in the art to divide the prism 22 by a longitudinal section such that the part of the prism above the mirror surface area 32 constitutes a reference light prism 22' and the part above the measuring light area 33 of the prism 22 constitutes a measuring light prism 22". The reference light prism 22' and the measuring light prism 22" are disposed side by side such together they form the common prism 22. This arrangement preferably is secured together by suitable glue or cement. Any suitable adhesive material used to glue together optical elements of glass or the like may be used; for example a glue dyed black may help to suppress the risk of mutual light influences by scattering in the optical material. The interface between the reference light prism 22' and the measuring light prism 22" is demonstrated in the sectional elevation of FIG. 2 by a dividing line 23.

The presentation of FIG. 3 is a diagrammatic top view of the modified embodiment showing the reflecting surface 60' and the part-wedge 40' placed on top. In this presentation the reflecting surface 60' or the preferably mirror-like surface 60' corresponds in width to the measuring light area 33 of the measuring light prism 22", while the width of the part-wedge 40' corresponds to the width of the reference light prism 22'. This provides a wedge separating line 53 corresponding to a part-wedge sidewall which faces the reflecting or mirror-like surface 60'. In correspondence with the length of the part-wedge 40', a front surface 55 of the part-wedge 40' becomes displaced vertically with respect to the wedge separating line 53 along a dash-dot line 53', the preferred length of the part-wedge extending up to the shield 46.

FIG. 4 shows another embodiment of the invention similar to FIG. 1. As corresponding structural elements are designated by corresponding reference numerals, prism 22 of FIG. 1 is replaced by prism 122 of FIG. 4, reference light beam 56 of FIG. 1 by reference light beam 156 of FIG. 4, measuring light beam 58 of FIG. 1 by measuring light beam 158 etc. In other words, structural elements and designations provided with the same reference numerals in the drawings have the same function each, they differ only by the respective hundred and the particular realization.

In the case of the embodiment shown in FIG. 4 the light source 110 is a controlled semiconductor light source disposed in a light generating apparatus 113. This apparatus houses another light source 111 which is displaced in space with respect to the first light source 110, preferably by 90°, to emit its light on to a partly transparent mirror 166 which, preferably, is semi-transparent. Other ratios of division depend on the design of the two light sources 110 and 111. The light beam emitted by the light source 110 fully passes through the partly transparent mirror 166, yet the light beams emitted by the second light source 111 are reflected at the partly transparent mirror 166 such that in the subsequent optical path both light beams will follow the same path.

The two light sources 110 and 111, preferably having different wave length band widths, are controlled alternatingly or simultaneously by a control means 109, depending on the particular use of the refractometer.

As shown in FIG. 4, the light produced by the light generating apparatus 113 passes through a preferably provided ground glass disc 112 and preferably a convex lens 114 onto a mask-like diaphragm 116 which has its masking function adapted to the task of the refractometer. In response to the particular dispostion, the light beams 154 generated by the light generating apparatus 113 impinge as a whole or divided on a directional mirror 118 which directs the light beams 154 on to an input lens 120 positioned at the entry of the prism 122, provided such an input lens 120 is desirable in view of the particular function of the refractometer.

As with the embodiment according to FIG. 1, the light beams 154 are divided by the corresponding mirror surface area at the prism base area 124 or at the active surface area 134 of the sapphire disc 126 and directed through the output lens 138 preferably provided on to a separating mirror 161. Thus the reference light beam 156 and the measuring light beam 158 are formed, the latter depending in intensity on the respective sample 130.

The separating mirror 161 has the same function as the light refracting wedge 40 in the arrangement of FIG. 1, the angle included by the wedge being reduced to zero.

FIG. 5 is a presentation similar to FIG. 3 showing a top plan view of the separating or dividing mirror 161 comprising two areas separated by a black separating face 157. The width of the black separating face 157 is selected in accordance with the respective application of the refractometer. In the extreme case it may be reduced to a separating line. The two areas formed by the separating face 157 are a reference light area 144 and a light measuring area 160.

The reference light beam 156 incident on the reference light area preferably is directed towards the evaluator 150 by means of a converging lens 163. The measuring light beam 158, of which the light intensity varies, is deflected in the reflecting measuring light area 160 and also passes through a converging lens 162 on to a receiver 164. The embodiment according to FIG. 4 comprises a shield 146 shielding the measuring light beam in chamber-like fashion from the reference light beam 156 and any other influences.

Preferably the evaluator 152 and the measuring light receiver 164 are installed in a retaining means 151 under controlled temperature, as shown in FIG. 6. FIG. 6 also discloses how the measuring light beams 158 and the reference light beams 156 are received shifted in space.

Figures 7, 8:
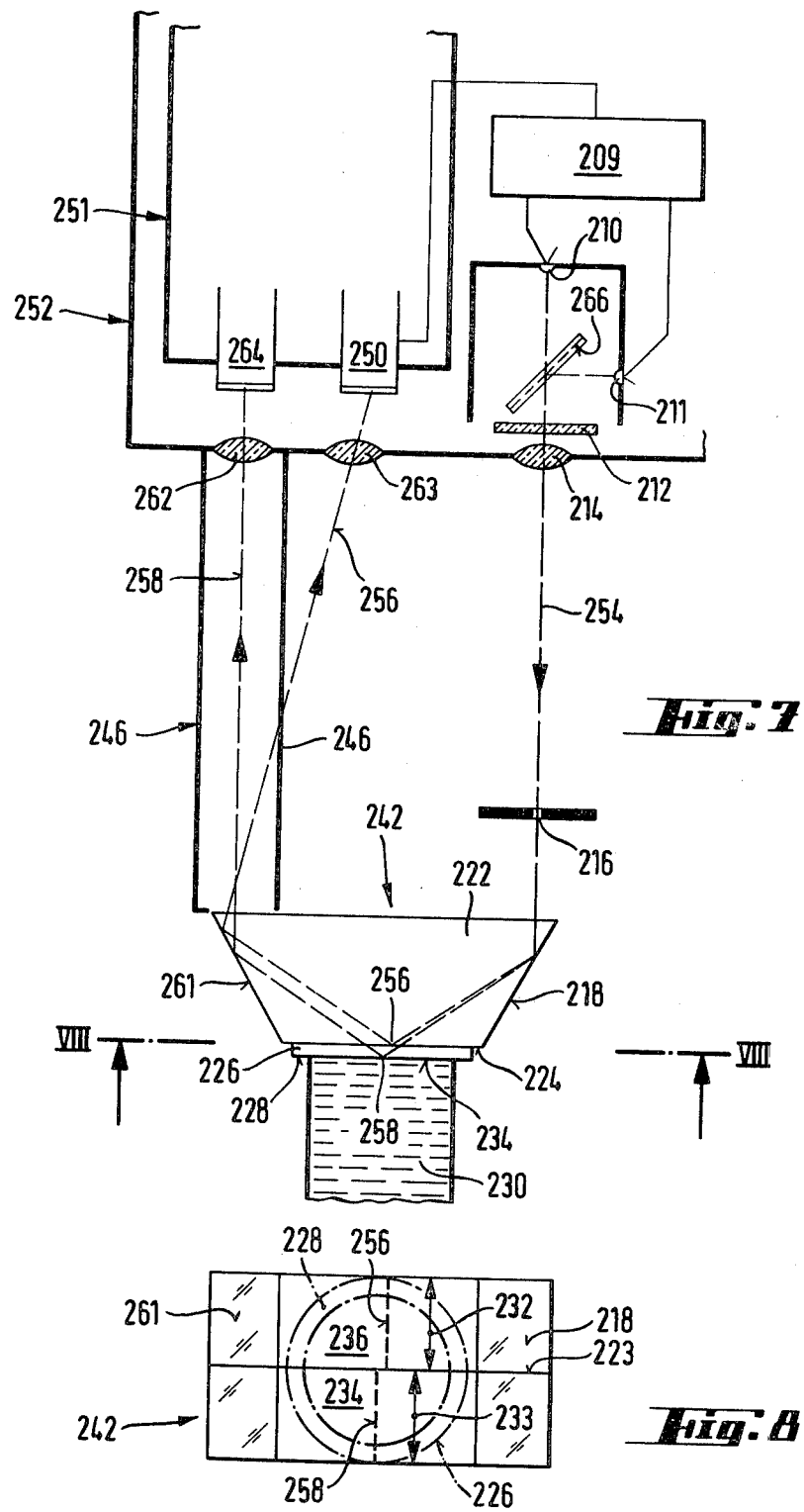
FIG. 7 is a view similar to FIGS. 1 and 4 of another embodiment of the invention in which a novel integral prism body is provided.
FIG. 8 is a sectional view of the novel integral prism body along the active boundary face of FIG. 7.

FIG. 7 shows another embodiment of the invention, illustrating the prismatic body 222 rotated through 180° with respect to the presentation of the prismatic body 122 in FIG. 4 or 22 in FIG. 1 so that the base of the prismatic body 222 is at the top and the side opposite to the base constitutes the base area 224 as regards the function of the prismatic body 222. As with the other embodiments, the sapphire disc 226 is mounted on this base area 224. In the embodiment according to FIG. 7 the directional mirror 118 of FIG. 4 or 18 of FIG. 1 is integrated in the oblique face of the prism 222 such that the incident light from the light generating apparatus 213 is deflected at the oblique prism face 218 and directed to the mirror-surface reference light area 232 or the measuring light area 233. From these areas the reference light 256 impinges on a separating mirror surface 261 which corresponds to the separating mirror surface 161 shown in FIG. 4 and which is formed by the other limiting face of the prism. In similar manner the measuring light beam 258, the intensity of which is influenced by the sample 230, passes from the active limiting face 234 to the other area of the separating mirror 261 and then, while being protected by the shield 246, through a converging lens 262 on to receiver 264, whereas the reference light beam 256 passes from the reference light area of the separating mirror 261 through a converging lens 263 on to the reference light receiver 250.

FIG. 8, which essentially resembles the presentation of FIG. 2, shows a section along the active limit face 234, from a view directed away from the sample 230. The prismatic body 242 may also be divided at the separating line 223, as described above. With the embodiment according to FIGS. 7 and 8 the reference light area is just about as wide as the measuring light area 233, the width of the respective areas also being selected in accordance with the particular problem to be solved by the refractometer.

The measuring light receiver 264 and the reference light evaluator are connected to a suitable electronic circuit to which also the control means 209 is connected which serves to influence the light sources 210 and 211.

It is within the scope of the general skill in the art to provide terminals for a plurality of displays to represent not only the various operational phases but to connect also recording and logging equipment. What is important with the instant invention is the principle of automatic temperature compensation of the measuring system by the joint treatment provided of the reference and measuring light beams whereby the temperature influences of the medium under examination on the measuring system are balanced.

What we claim is:

1. A refractometer for measuring refractive index of a media during a continuous process comprising:

light source means for producing a light beam, a light prismatic body having a media surface contacting the boundary surface of said media and a mirror surface, said light beam being directed onto said mirror surface and said media surface to provide a reference light beam reflected from said mirror surface and a measurement light beam reflected from said boundary surface, first means for receiving said reference beam and producing an electrical signal varying as a function thereof, second means for receiving said measurement beam and producing an electrical signal varying as a function thereof, and means for directing said reference and measuring beams respectively to said first and second means.

2. A refractometer as in claim 1 wherein said body includes a light transmitting disc having a surface in contact with said boundary and a prism having a mirror surface in contact and fixed to the opposite surface of said disc.

3. A refractometer as in claim 2 wherein said body further includes a first plane-convex lens fixed to a surface of said prism for transmitting said beam onto said mirror surface and said media surface and a second plane-convex lens fixed to a surface of said prism for transmitting said reference beam and said measurement beam to said directing means.

4. A refractometer as in claim 1 wherein said disc is sapphire.

5. A refractometer as in claim 1 wherein said directing means includes a light refracting wedge disposed in the light path of said reference beam and said measurement light beam.

6. A refractometer as in claim 5 wherein said wedge has a mirror surface at the side facing the incoming light to reflect the reference beam and a surface on the opposite side to reflect the measurement beam.

7. A refractometer as in claim 1 wherein said body has a rectangular base area and a circular sapphire disc mounted on said base area and having an active surface area in contact with said boundary surface and smaller than the area of said disc.

8. A refractometer as in claim 7 wherein said mirror surface extends in the form of a rectangle along a marginal zone of the base area and covers part of said disc.

9. A refractometer as in claim 8 wherein said directing means includes a light refracting wedge disposed in the light path of said reference beam and said measurement light beam and having a mirror surface at the side receiving the incoming light to reflect the reference beam, and wherein the mirror surface of said wedge extends in the form of a rectangle along a marginal zone.

10. A refractometer as in claim 9 wherein the width of the marginal zone at the wedge corresponds to the width of the marginal zone at the prism.

11. A refractometer as in claim 10 further including a shield disposed at least partly between the light paths of the measurement and reference light beams.

12. A refractometer as in claim 11 wherein the mirror surface in the marginal zone of the wedge extends up to the shield.

13. A refractometer as in claim 12 wherein said wedge is made of glass.

14. A refractometer as in claim 1 wherein said wedge is made of glass.

15. A refractometer as in claim 1 wherein said second means includes first and second light detectors and means for splitting the light from said means for directing into two beams and for directing the two beams to said first and second light detectors respectively.

16. A refractometer as in claim 15 wherein said splitting means is a partly reflecting mirror with a transparent to reflecting ratio of 50:50.

17. A refractometer as in claim 1 wherein said light source is variable in brightness.

18. A refractometer as in claim 1 wherein said light source is a wide spectrum halide lamp.

19. A refractometer as in claim 1 including means for controlling said light source in accordance with the output of said first means.

20. A refractometer as in claim 1 wherein said prismatic body is made of a reference light prism and a measuring light prism.

21. A refractometer as in claim 20 wherein said prisms are glued together.

22. A refractometer as in claim 1 wherein said directing means includes a light reflecting wedge disposed in the light path of said reference and measurement light beams and mounted on a carrier.

23. A refractometer as in claim 22 wherein the width of said wedge corresponds to the width of said mirror surface and wherein the carrier surface reflects the measurement beam.

24. A refractometer as in claim 1 wherein said directing means includes a separating mirror divided into a reference light mirror area and a measurement light mirror area.

25. A refractometer as in claim 24 wherein the reference light area of the separating mirror has a width corresponding to the width of the mirror surface area of the body.

26. A refractometer as in claim 25 wherein said directing means further includes a shield mounted on said separating mirror for guiding the reference and measurement light beams.

* * * * *